United States Patent [19]

Chakrabarti

[11] 4,165,367
[45] Aug. 21, 1979

[54] HAIR PREPARATIONS CONTAINING VINYL PYRROLIDONE COPOLYMER

[75] Inventor: Paritosh M. Chakrabarti, Wayne, N.J.

[73] Assignee: GAF Corporation, New York, N.Y.

[21] Appl. No.: 805,396

[22] Filed: Jun. 10, 1977

[51] Int. Cl.² .......................... A61K 7/06; A61K 7/11
[52] U.S. Cl. ...................................... 424/47; 8/127.51;
424/DIG. 1; 424/DIG. 2; 424/70; 424/71
[58] Field of Search .................. 424/DIG. 1, DIG. 2,
424/47, 70, 71; 8/127.51

[56] References Cited
U.S. PATENT DOCUMENTS

| 3,144,391 | 8/1964 | Goff | 424/47 X |
| 3,145,147 | 8/1964 | Glickman | 424/47 |
| 3,423,367 | 1/1969 | Merijan et al. | 424/47 X |
| 3,530,215 | 9/1970 | Grief et al. | 424/71 X |
| 3,910,862 | 10/1975 | Barabas et al. | 424/71 X |
| 3,914,403 | 10/1975 | Valan | 424/47 |
| 3,954,960 | 5/1976 | Valan | 424/47 |
| 3,980,769 | 9/1976 | Ghilardi et al. | 424/70 |
| 3,996,146 | 12/1976 | Farasov et al. | 424/70 X |
| 4,035,478 | 7/1977 | Mullen | 424/70 |

Primary Examiner—Bernard Helfin
Assistant Examiner—Vera C. Clarke
Attorney, Agent, or Firm—Walter C. Kehm

[57] ABSTRACT

Hair preparations containing a copolymer of about 95 to 45 mole percent of vinyl pyrrolidone and about 5 to 50 mole percent of diloweralkylaminoalkyl acrylate or methacrylate, and method of setting and conditioning hair therewith.

15 Claims, No Drawings

HAIR PREPARATIONS CONTAINING VINYL PYRROLIDONE COPOLYMER

This invention relates generally to cosmetic peparations and especially to hair setting and conditioning compositions containing certain copolymers of vinyl pyrrolidone (N-vinyl-2-pyrrolidone), hereafter referred to as VP.

In the field of hair care, setting, waving, conditioning and the like, broad types of hair treating preparations have been proposed, the principal ones being cationic surfactants, superfatting materials, water soluble proteins and synthetic polymers, in a suitable cosmetically acceptable medium. The synthetic polymer containing preparations are generally regarded as most effective, particularly those containing water soluble cationic polymers which are substantive to hair and exhaust thereon from solution or diluent medium. British Pat. No. 1,331,819 and U.S. Pat. Nos. 3,910,862 and 3,954,960, the disclosures of which are incorporated herein for reasons which will become apparent, describe water soluble cationic quaternized copolymers of VP and a dialkylaminoalkyl acrylate or methacrylate, and hair care compositions containing such copolymers which have been found to be highly effective in providing most of the properties considered necessary in the theoretically perfect hair preparation, as in fact also described in said patents. The hair preparations described in said patents are however not optimal in certain respects, as for example cost of producing the quaternized copolymers, and a curl retention under high humidity conditions.

It is an object of this invention to provide hair treating compositions which will not be subject to one or more of the above disadvantages. Another object of the invention is the provision of such compositions containing lower-cost copolymers.

Still another object of the invention is the provision of hair setting and conditioning compositions with improved curl retention under high humidity conditions. Yet a further object of the invention is the provision of an improved method of treating, setting and/or conditioning hair (human hair on or off the head as in wigs) with such compositions. Other objects and advantages will appear as the description proceeds.

The attainment of one or more of the above objects is made possible by this invention which includes the provision of A hair setting and conditioning composition comprising, approximately by weight, I. 0.1 to 35% of a film-forming copolymer having a molecular weight of about 15,000 to 1,500,000 and containing
   A. about 95 to 45 mole percent of units derived from vinyl pyrrolidone
   B. about 5 to 50 mole percent of units derived from a monomer of the formula

wherein
   $R^1$ is H or $CH_3$,
   $R^2$ is $C_{1-20}$ alkylene, and
   $R^3$ and $R^4$ are independently $C_{1-4}$ alkyl, and
   C. 0 to about 50 mole percent of units derived from at least one ethylenically unsaturated copolymerizable monomer different from A and B, II. 0.05 to 10% of at least one cosmetically acceptable member of the group consisting of organic surface active agents, thickening agents, plasticizers and sequestering agents, in III. a solvent base selected from the group consisting of water, monohydric $C_{2-3}$ aliphatic alcohols, 1,1,1-trichloroethane, methylene chloride, and mixtures thereof.

In the above monomer B formula, $R^2$ may for example be methylene or preferably ethylene or may be branched or isomeric but preferably normal or linear hydroxyethylene, propylene, hydroxypropylene, butylene, pentylene, hexylene, heptylene, octylene, nonylene, decylene, dodecylene, tetradecylene, hexadecylene, octadecylene or di-decylene; and $R^3$ and $R^4$ may be independently butyl, t-butyl, isobutyl, propyl, isopropyl, ethyl, or preferably methyl.

The optional monomer C may be any conventional vinyl or vinylidene monomer other than B copolymerizable with A (VP). Exemplary of such monomers are the alkyl vinyl ethers, e.g. the methyl, ethyl, octyl and lauryl vinyl ethers; acrylic and methacrylic acid and esters thereof, e.g. methyl acrylate, ethyl acrylate and methyl methacrylate; vinyl aromatic monomers, e.g. styrene and alpha-methyl styrene; vinyl acetate and chloride; vinylidene chloride; acrylonitrile and methacrylonitrile and substituted derivatives thereof; acrylamide and methacrylamide and N-substituted derivatives thereof; crotonic acid and esters thereof, e.g. methyl and ethyl crotonate; and the like.

The above mentioned U.S. patents disclose the production of quaternized derivatives of polymers containing the above-defined A, B and optional C units but with B present in proportions of about 5 to 80 mole percent. The above-mentioned Brit. Pat. No. 1,331,819 contains a similar disclosure but with B being present in proportions of 1 to 80 mole percent. It was highly surprising to discover that elimination of the quaternization step required in accordance with the teachings of said patents not only did not result in any significant detriment to the properties of the hair preparations containing such polymers but proved advantageous in substantially reducing the costs of manufacture and in providing hair preparations yielding improved properties in the treated hair with respect to improved curl retention under high humdity conditions, among other miscellaneous advantages.

It should accordingly be understood that the method of making the copolymers employed herein, by free radical addition polymerization, preferably in aqueous or alcoholic (e.g. ethanol, isopropanol) solution, and examples of the acrylate or methacrylate monomer B and the optional ethylenically unsaturated (vinyl or vinylidene) monomer C employed in such method, are adequately disclosed in said patents, subject to the use of 5 to 50 mole percent of monomer B. As monomer B, di-$C_{1-2}$ alkylaminoethyl acrylates and methacrylates are preferred, especially dimethylaminoethyl methacrylate. Any of the other dialkylaminoalkyl acrylates and methacrylates disclosed in U.S. Pat. No. 3,910,862 at column 3, line 56 to column 4, line 15, may however be employed, in addition to their substantial equivalents in which the terminal dialkyl groups ($R^3$ and $R^4$) taken together form with the bonded N atom a 5 or 6 membered heterocyclic ring such as morpholino, methyl piperidino, pyrrolidono, and the like. Monomer B preferably constitutes about 5 to 40, more preferably about 10 to 30, mole percent of the above-defined polymer I of the present invention. Correspondingly, polymer I preferably contains about 95 to about 60, more preferably about 90 to 70 mole percent of units derived from VP (monomer A).

Similarly, any of the monomers disclosed in British Pat. No. 1,331,819 at page 2, lines 65–82, may be employed to provide the optional ethylenically unsaturated copolymerizable monomer C units in said polymer I.

The copolymers employed according to the present invention can be prepared over a wide range of molecular weights, e.g. from about 15,000 to 1,500,000 or more, depending upon the particular choice of reactants, initiator, solvent and polmerizing conditions, lower temperatures being generally conducive to the formation of higher molecular weight copolymers. The desired molecular weight range in any particular instance will in general be influenced by the type, utility, and dispensing method of the cosmetic composition in which it will be employed. Since these copolymers are soluble in both water and alcohol, they can be employed in cosmetic compositions, particularly hair preparations, containing an alcoholic, aqueous or mixed aqueous-alcoholic base or carrier. The preferred higher molecular weight copolymers of about 500,000 to 1,500,000 or more in addition act as their own thickeners, aqueous and/or alcoholic solutions displaying a slippery feel and facilitating application, local or overall, to the hair.

The above described copolymers of this invention can be employed in hair preparations and other cosmetic compositions in the same manner and with the same surface active agents, thickening agents, plasticizing agents and sequestering agents as the heretofore employed conventional film-forming resins, for example with the same additives and in the same formulations as disclosed for the quaternized copolymer in U.S. Pat. No. 3,954,960. They may generally be formulated for hair setting, waving, conditioning, shampooing, coloring, and/or bleaching functions in the form of a lotion, cream (paste), gel, pump spray or pressurized aerosol. Conveniently, the copolymer is dissolved, generally in proportions of about 0.1 to about 5%, preferably about 0.2 to about 2%, by weight of the formulation, in the solvent of choice, e.g. 1,1,1-trichloroethane, methylene chloride, or preferably ethanol, isopropanol, 2-methoxyethanol, or water or mixtures thereof, in the presence of (before, with or after addition of) about 0.05 to about 10% by weight of one or a mixture of the known, conventional, cosmetically acceptable organic surface active agents, thickening agents, plasticizing agents and sequestering agents.

As organic surface active agents useful in the cosmetic, particularly hair, preparations of this invention, any one or more of the anionic, ampholytic, polar nonionic, zwitterionic and cationic organic surfactants disclosed in U.S. Pat. No. 3,489,686 at column 2, line 66 to column 5, line 2 may be employed.

As operative thickening agents there may be mentioned carboxymethylcellulose, hydroxyethylcellulose, methylcellulose, magnesium aluminum silicate, Carbopols (B. F. Goodrich) such as Carbopol 940, and the like. Useful sequestering agents include sodium ethylenediaminetetracetates, polyphosphates and nitrilotriacetates, corresponding potassium salts, etc.

As useful plasticizing agents (including emollients, lubricants), there may be mentioned lanolin and lanolin derivatives such as acetylated and ethoxylated lanolin alcohols and isopropyl lanolate, polyoxyethylenated sorbitan monooleate, trioleate and monostearate, ethylene, diethylene, propylene and hexylene glycols and their monomethyl and monoethyl ethers and monoacetates, glycerin, glycerol triacetate and monoricinoleate, long chain alcohols such as oleyl, isostearyl and cetyl alcohols and their polyoxyethylenated derivatives, e.g. with 2–30 moles of ethylene oxide, dimethyl, diethyl and dibutyl phthalates, triethylphosphate, isopropyl myristate and palmitate, dimethyl and methylphenyl polysiloxane and other silicones, and the like.

Certain volatile plasticizers may also be employed such as propionamide, benzoic and salicylic acid, menthol, thymol, methyl-2-naphthylketone, hexachloroethane, benzophenone and acetamide.

Other optional conventional additives include opacifiers, colorants, perfumes, UV absorbers, preservatives, medicaments, suds boosters or depressants, penetrants, lustrants, deodorants and the like.

The compositions may also be employed for other cosmetic purposes such as hand lotions, deodorant sprays and lotions, protective and moisturizing creams, etc.

The present invention includes a method comprising treating hair with an aqueous, alcoholic, or aqueous-alcoholic medium containing an effective amount of the above-defined copolymer I, such amount depending of course upon the desired function, e.g. conditioning, bodying, lusterizing, shape setting and holding, rinsing, protecting, improving manageability and the like, and generally ranging from about 0.1 to 5%, preferably about 0.2 to 2%, by weight in said medium. Such medium desirably also contains conventional hair preparation additives such as about 0.05 to about 10% of one or more of the above-mentioned cosmetically acceptable agents, i.e. surfactants, thickeners, plasticizers and sequesterants, in addition to other such conventional additives including those described elsewhere herein These copolymers are substantially more substantive to hair relative to corresponding copolymers containing less than 5 mole percent of monomer B, such degree of substantivity varying (increasing) directly with the proportion of monomer B in the copolymer. They are accordingly especially advantageous for use in rinse-type hair conditioning applications and conditioning shampoos. Thus, for rinse type applications, the copolymer in the aqueous and/or alcoholic medium may contain about 5 to 20, preferably about 10 to 15, mole percent of monomer B units, the substantivity of the copolymer to the hair being treated preventing it from being lost in the rinsing liquid. Because of such substantivity, dilute solutions of the copolymer may if desired be employed. When it is desired to use these copolymers as conditioning agents in shampoos, the copolymer should contain at least about 15, preferably about 15 to 30, mole percent of monomer B units. These higher proportions of monomer B units are necessary to enable effective deposition on the hair of the copolymer from the shampoo vehicle which, because of its relatively high content of detergents, tends to wash out the copolymer conditioner from the hair.

In general, for use in the form of a lotion, cream or gel for conditioning, bodying, lusterizing, shape setting and holding (curling, waving, straightening, shaping), improving manageability (combability, brushability, shaping), protectors against mechanical and chemical influences, and the like, the invention involves the treatment of human hair with a lotion, cream or gel containing, approximately by weight, 0.1 to 5% of the above-defined polymer I in 99.9 to 95% of a solvent medium, 50 to 100% of which is water and 0 to about 50% of which is at least one $C_{2-3}$ aliphatic monohydric alcohol, desirably with 0.05 to 10% of said medium being replaced by at least one cosmetically acceptable organic surface active agent, thickening agent, plasticizing agent or sequestering agent. In most instances, the lotion, cream or gel composition contains about 0.05 to 1.0% of at least one surface active agent and 0.1 to 1.0% of a thickener.

For application in the form of a pump spray, about 3 to about 70% of said solvent medium is composed of said alcohol to facilitate the spray function and hasten drying.

For application as a conditioning rinse, said solvent medium is generally devoid of alcohol, desirably with about 0.05 to 10% of said medium being replaced by at least one of said cosmetically acceptable agents. In most instances the conditioning rinse contains about 1.5 to 10% of at least one surface active agent and 0 to about 4% of at least one plasticizer, e.g. glycerolstearate.

For application as a conditioning shampoo, said solvent medium is also generally devoid of alcohol which acts as a foam or suds depressant, with about 10 to 50% of said medium being replaced by at least one surface active agent acting as detergent, and desirably with about 0.05 to 10% of said medium being replaced by at least one cosmetically acceptable thickener, plasticizer or sequestrant, especially the plasticizer, e.g. polyethylene glycol (6000) stearate and/or propylene glycol. One or a mixture of two or more of the surface active agents disclosed in U.S. Pat. No. 3,489,686, as indicated above, any function as the detergent component in the shampoo.

A pressurized aerosol formulation according to the invention may contain, approximately by weight, 0.1 to 5% of said copolymer I, 0 to 10% of one of the aforesaid agents, 25 to 60% of the aforesaid alcohol, 0 to 40% of water, and 10 to 70% of propellant.

In the above formulations, all or part of the alcohol may be replaced by 1,1,1-trichloroethane or methylene chloride or the like, and concentrates containing up to 35% or more of the copolymer may be produced and used.

Any propellant may be employed for pressurizing the aerosol in its valved pressure container, pressurized or liquified gas or the like. For example, where not prohibited, any of the known chlorofluoro hydrocarbons, or mixtures thereof, may be employed, if desired in admixture with other types of propellants such as described below. Freons 11, 12 and 114, particularly dual mixtures thereof, are useful, in addition to other Freons and their counterparts available as Genetrons, Isotrons, etc. Other useful propellants include any or a mixture of normal and isopreopanes and butanes, nitrogen, nitrous oxide, carbon dioxide, and the like.

The VP copolymers employed herein have a number of important advantages relative to prior art hair setting and conditioning resins, including:
1. Complete water solubility under all pH conditions.
2. Amenability to yield clear aqueous, alcoholic, or aqueous-alcoholic liquid formulations.
3. Lower cost, particularly as compared with their quaternized derivatives.
4. Superior hair holding power under high humidity conditions.

The compositions of the present invention are particularly useful for the following distinctive on-hair performance criteria:
1. Good adhesion and spreading on hair.
2. Detangling of wet hair.
3. Provides hair with a lustrous "natural" as against a dirty "coated" appearance.
4. Adds body and a lively bounce to hair.

The copolymer I employed herein may, as indicated above, be prepared by the procedures disclosed in U.S. Pat. No. 3,910,862, omitting of course the final quaternizing step, e.g. Examples 1 to 4 and 6 of said patent.

As also indicated above, the copolymer I of this invention may be substituted for the quaternized copolymers employed in the various formulations exemplified in U.S. Pat. No. 3,954,960, e.g. Examples 2 to 10. The following additional examples are only illustrative of further preferred embodiments of this invention and are not to be regarded as limitative. In these examples and the appended claims all amounts and proportions are by weight unless otherwise indicated, DMAEMA is dimethylaminoethyl methacrylate, the VP/DMAEMA 90/10 has a number average molecular weight (M.W.) ranging from about 700,000 to at least 1,000,000, the VP/DMAEMA 80/20 has a M.W. range of about 1,000,000 to 1,500,000, "Ethoquat" indicates quaternization with diethylsulfate, such quaternized derivatives have the same M.W. range as the non-quaternized precursors, PVP K90 (VP homopolymer) has a M.W. of about 360,000 and PVP K30 has a M.W. of about 40,000.

The following test procedure used in these examples was developed to compare the hair-holding qualities of different products under varying temperature and humdity conditions:

Humdity Curl Retention Test

1. Human, untreated hair is used for this test.
2. A master shank of hair is subdivided into a series of individual swatches each nine inches long and weighing 1.5 grams.
3. A minimum of 6 swatches is used for each product to be evaluated.
4. In each case 1.2 ml. of the product is used per hair swatch. The product is worked down into the swatch so as to give a uniform application throughout the entire swatch.
5. Each swatch is combed twice immediately after product application. It is then curled using a ⅝" O.D. mandril and pinned.
6. The swatches are then thoroughly dried using a salon hair dryer at high temperature setting approximately 1½ hours.
7. The humidity chamber is preconditioned to the desired temperature and humidity.
8. After drying, the swatches are unpinned and carefully opened. Each swatch is individually mounted on a precalibrated plexiglass board. The initial length is recorded. The swatches are so spaced so no one cell will have an abnormal number of swatches in any one area of the humidity chamber.
9. The plexiglass boards are then placed in the humidity chamber. The temperature and relative humidity are recorded.
10. Swatch length readings are taken at various prescribed time intervals with the corresponding temperature and relative humidity recorded.

11. The data for each product obtained on the six or so swatches are averaged for comparison purposes.
12. Since the test is dependent upon the nature of hair used, cross comparison between two different lots of hairs is not meaningful.

Although left-on-the-hair type formulations containing the copolymers employed in the present invention have been discussed above, such formulations and uses thereof are less preferred since, because of the relatively greater substantivity of such copolymers for hair, there will be a greater tendency towards resin buildup on the treated hair which of course may not be considered objectionable by some. The following examples illustrate the preferred embodiments of this invention involving use of the copolymer in rinse type conditioners, conditioning shampoos, and aqueous media, in addition to the less preferred embodiments.

EXAMPLE 1

This example compares the curl retention values of copoly VP/DMAEMA (90/10), copoly VP/DMAEMA (80/20) and PVP K-30 (the most preferred grade of PVP for hair cosmetic application) under identical conditions. All these polymers are tested at 2% solids level from an aqueous medium.

| Product | % Curl Retention 90% RH and 80° F. | | | |
|---|---|---|---|---|
| | 0 min. | 30 min. | 60 min. | 90 min. |
| PVP K-30 | 100 | 34 | 8 | 4 |
| 90/10 VP/DMAEMA | 100 | 100 | 93 | 76 |
| 80/20 VP/DMAEMA | 100 | 100 | 97 | 91 |

The above results show that the VP/DMAEMA copolymers of this invention are significantly superior to the polyvinylpyrrolidone homopolymers with respect to curl retention under high humidity conditions.

EXAMPLE 2

This example shows that the copolymers of the current invention have superior humidity holding characteristics over their quaternary derivatives disclosed in prior art.

The two copolymers, VP/DMAEMA (90/10) and VP/DMAEMA (80/20), are tested against their ethoquats made from the same samples according to prior teachings (USP 3,910,862) under identical conditions employing 2% aqueous solutions of the copolymers. The results are as follows:

| Product | % Curl Retention 88% RH, 80° F. | | | |
|---|---|---|---|---|
| | 0 min. | 30 min. | 60 min. | 90 min. |
| VP/DMAEMA (90/10) | 100 | 100 | 96 | 69 |
| Quat of above | 100 | 100 | 87 | 52 |
| VP/DMAEMA (80/20) | 100 | 100 | 96 | 86 |
| Quat of above | 100 | 100 | 94 | 69 |

EXAMPLE 3

| Cream Rinse | Parts |
|---|---|
| Arquad 2 HT-75 * | 7.5 |
| Glyceryl monostearate | 2.0 |
| VP/DMAEMA 90/10 | 0.4 |
| Distilled water | 90.0 |
| Glutaraldehyde | 0.1 |
| Citric Acid | Q.S. to pH 5.0-5.5 |

* Armak - cationic dimethyl di(hydrogenated tallow) ammonium chloride, 75% active.

EXAMPLE 4

| Cream Rinse | Parts |
|---|---|
| Triton X400 * | 7.0 |
| Glyceryl monostearate | 2.0 |
| Ceraphyl 28 ** | 1.0 |
| VP/DMAEMA 90/10 | 0.5 |
| Distilled water | 90.0 |
| Glutaraldehyde | 0.4 |
| Sodium hydroxide | Q.S. to pH 5.0-5.5 |

* Rohm and Haas - cationic stearyl dimethyl benzyl ammonium chloride, 25% solids
** Van Dyke - cetyl lactate

EXAMPLE 5

| Clear Cream Rinse | Parts |
|---|---|
| VP/DMAEMA 80/20 | 0.2 |
| Ammonyx KP * | 4.0 |
| Natrosol HHR ** | 0.4 |
| Distilled water | 95.4 |

* Onyx Chemical - cationic oleyl dimethyl benzyl ammonium chloride
** Hercules - hydroxyethyl cellulose

EXAMPLE 6

| Conditioning Shampoo | Parts |
|---|---|
| Miranol C2M * | 15.0-20.00 |
| Coconut diethanolamide | 4.0 |
| Propylene glycol | 7.0 |
| VP/DMAEMA 80/20 | 1.5 |
| PEG 6000 distearate ** | 5.0 |
| Dinonyl phenol + 150 E.O. | 5.0 |
| Water, distilled | Q.S. to 100 |

* Coconut imidazolinium-N-ethoxymethylcarboxy-N-acetic acid, disodium salt - Miranol Corporation.
** Armak - polyethylene glycol (6,000 M.W.) distearate.

EXAMPLE 7

| Conditioning Shampoo | Parts |
|---|---|
| Sipon LT6 * | 35.0 |
| Coconut diethanolamide | 4.0 |
| Ceraphyl 65 ** | 2.5 |
| VP/DMAEMA 90/10 | 0.5 |
| Perfume | 0.1 |
| Distilled water | Q.S. to 100 |

* Alcolac Chemical - triethanolamine lauryl sulfate
** Van Dyke Company - cationic mink oil-amidopropyl dimethyl 2-hydroxyethyl ammonium chloride.

EXAMPLE 8

| Conditioning Shampoo | Parts |
|---|---|
| Antaron PC-37 * | 8.0 |
| Antaron FC-34 ** | 15.0 |
| Maprofix ES *** | 13.5 |
| PEG 6000 Distearate | 3.1 |
| VP/DMAEMA 75/25 M.W. 500,000 | 1.0 |
| Sulfuric Acid | Q.S. to pH 7.4 |
| Distilled water | Q.S. to 100 |

* GAF Corporation - Amphoteric polyoxyethylenated quaternized sulfated fatty amine, 75% active.
** GAF Corporation - Foam boosting amphoteric monocarboxyl coco imidazoline, 38% active.
*** Onyx Chemical - anionic sodium lauryl polyoxyethylene (2-4E.O.) sulfate, 30% active.

EXAMPLE 9

| Wave Setting Gel | Parts |
|---|---|
| Carbopol 940 * | 0.75 |
| Uvinul MS-40 ** | 0.10 |
| Ethylenediaminetetraacetic acid disodium salt (0.1% aq.) | 0.10 |
| Triethanolamine | 1.00 |
| Water, distilled | 96.55 |
| VP/DMAEMA 90/10 (100% solids) | 1.50 |
| Color F.D.C. Yellow #5 (0.6%) | 0.3 |
| Fragrance | 0.1 |
| Preservative | 0.1 |

* B.F. Goodrich Chemical thickener - water soluble polymer of acrylic acid cross-linked with under 2% of a polyallylether of sucrose having an average of about 5-6 allyl groups per sucrose molecule.
** GAF Corporation UV absorber -2-OH-4-methoxybenzophenone-5-sulfonic acid.

EXAMPLE 10

| Wave Setting Gel | Parts |
|---|---|
| Carbopol 940 | 0.35 |
| Uvinul MS-40 | 0.10 |
| Ethylenediaminetetraacetic acid, disodium salt (0.1% aq.) | 0.10 |
| Triethanolamine | 0.50 |
| Water, distilled | 97.05 |
| VP/DMAEMA 80/20 (100% solids) | 1.50 |
| Opacifier * | 0.40 |
| Color F.D.C. Yellow #5 (0.6%) | 0.3 |
| Fragrance | 0.1 |
| Preservative | 0.1 |

* GAF Corporation - 70% styrene graft polymerized on 30% PVP.

EXAMPLE 11

| Pump Spray Conditioner (for Blow Drying) or Hair Spray (for Regular Use) | Parts |
|---|---|
| VP/DMAEMA 80/20 (100% solids) | 1.00 |
| Ammonyx 4002 * | 0.40 |
| Tween 20 ** | 0.20 |
| Fragrance | 0.1 |
| Ethanol | 60.00 |
| Water, distilled | 38.40 |

* Onyx Chemical - stearyl dimethyl benzyl ammonium chloride (100%).
** I.C.I. - Polyoxyethylene (20) sorbitan monolaurate.

EXAMPLE 12

| Pump Type Blow Dry Hair Conditioner | Parts |
|---|---|
| VP/DMAEMA 90/10 | 1.00 |
| Ammonyx KP * | 0.60 |
| Tween 20 | 0.20 |
| Perfume | 0.10 |
| Ethanol | 3.00 |
| Distilled water Q.S. to 100 | |

* Onyx Chemical - oleyl dimethyl benzyl ammonium chloride.

EXAMPLE 13

| Blow Dry Conditioner | Parts |
|---|---|
| VP/DMAEMA 90/10 | 1.00 |
| Carbopol 940 (100% solids) | 0.10 |
| Triethanolamine | 0.15 |
| Isostearyl alcohol + 10 E.O. | 0.05 |
| Tween 20 | 0.13 |
| Perfume | 0.20 |
| F.D.C. Yellow #5, (0.6% aq.) | 0.07 |
| Ethanol | 44.82 |
| Water, distilled | Q.S. to 100 |

EXAMPLE 14

| Aerosol Hair Spray | Parts |
|---|---|
| VP/DMAEMA 90/10 | 2.0 |
| Ethanol | 50.0 |
| Propellants | |
| Isobutane | 13.5 |
| Propane | 1.5 |
| Distilled water | Q.S. to 100 |

EXAMPLE 15

| Setting Lotion Concentrate | Parts |
|---|---|
| VP/DMAEMA 90/10 | 8.0 |
| PVP/VA E 735 * | 37.0 |
| Ammonyx KP | 2.4 |
| Tween 20 | 1.2 |
| Distilled water | Q.S. to 100 |

* GAF Corporation - 70 VP/30 Vinyl acetate copoymer, 50% in alcohol.

For use, dilute 1 part with 7 parts water.

This invention has been disclosed with respect to certain preferred embodiments and it will be understood that modifications and variations thereof obvious to those skilled in the art are to be included within the spirit and purview of this application and the scope of the appended claims.

What is claimed is:

1. A hair setting and conditioning composition comprising, approximately by weight,
   I. 0.1 to 35% of a film-forming copolymer having a molecular weight of about 15,000 to 1,500,000 and containing
      A. about 95 to 45 mole percent of units derived from vinyl pyrrolidone
      B. 5 to 50 mole percent of units derived from a monomer of the formula $$CH_2=CR^1-COOR^2-NR^3R^4$$

wherein
$R^1$ is H or $CH_3$,
$R^2$ is $C_{1-20}$ alkylene, and
$R^3$ and $R^4$ are independently $C_{1-4}$ alkyl, and
C. 0 to about 50 mole percent of units derived from at least one ethylenically unsaturated copolymerizable monomer different from A and B,
II. 0.05 to 10% of at least one cosmetically acceptable member selected from the group consisting of organic surface active agents, thickening agents, plasticizers and sequestering agents, in
III. a solvent base selected from the group consisting of water, monohydric $C_{2-3}$ aliphatic alcohols, 1,1,1-trichloroethane, methylene chloride, and mixtures thereof.

2. A pressurized aerosol hair spray containing about 10 to 70% of a propellant and a hair setting or conditioning amount of a composition as defined in claim 1.

3. A pressurized aerosol hair spray as defined in claim 2 wherein copolymer I consists essentially of units derived from vinyl pyrrolidone and dimethylaminoethyl methacrylate.

4. A hair conditioning shampoo containing, approximately by weight, 10 to 50% of at least one organic anionic, cationic, nonionic or amphoteric detergent and a conditioning amount of a composition as defined in claim 1.

5. A hair shampoo as defined in claim 4 wherein copolymer I consists essentially of units derived from vinyl pyrrolidone and dimethylaminoethyl methacrylate.

6. A composition as defined in claim 1 wherein copolymer I consists essentially of units derived from vinyl pyrrolidone and dimethylaminoethyl methacrylate.

7. A method for setting or conditioning hair comprising applying to the hair an effective amount of a composition as defined in claim 1.

8. A method for setting or conditioning hair comprising applying to the hair an effective amount of a composition as defined in claim 2.

9. A method for setting or conditioning hair comprising applying to the hair an effective amount of a composition as defined in claim 3.

10. A method for setting or conditioning hair comprising shampooing the hair with an effective amount of a composition as defined in claim 4.

11. A method for setting or conditioning hair comprising shampooing the hair with an effective amount of a composition as defined in claim 5.

12. A method for setting or conditioning hair comprising applying to the hair an effective amount of a composition as defined in claim 6.

13. A method for setting or conditioning hair comprising applying to the hair an aqueous, alcoholic, or aqueous-alcoholic medium containing an effective hair setting or conditioning amount of a film-forming copolymer having a molecular weight of about 15,000 to 1,500,000 and containing:
A. about 95 to 45 mole percent of units derived from vinyl pyrrolidone,
B. 5 to 50 mole percent of units derived from a monomer of the formula:

$$CH_2=CR^1-COOR^2-NR^3R^4$$

wherein $R^1$ is H or $CH_3$,
$R^2$ is $C_{1-20}$ alkylene, and
$R^3$ and $R^4$ are independently $C_{1-4}$ alkyl, and
C. 0 to about 50 mole percent of units derived from at least one ethylenically unsaturated copolymerizable monomer different from A and B.

14. A method as defined in claim 13 wherein said copolymer consists essentially of units derived from vinyl pyrrolidone and dimethylaminoethyl methacrylate.

15. A method as defined in claim 13 wherein said medium contains about 0.5 to 5% by weight of said copolymer.

* * * * *